US012364591B2

(12) United States Patent
Litvin et al.

(10) Patent No.: US 12,364,591 B2
(45) Date of Patent: Jul. 22, 2025

(54) KERATOPROSTHESIS DEVICES AND KITS AND SURGICAL METHODS OF THEIR USE

(71) Applicant: CORNEAT VISION LTD, Ra'anana (IL)

(72) Inventors: Gilad Litvin, Moshav Sde Varburg (IL); Almog Aley-Raz, Moshav Sde Varburg (IL)

(73) Assignee: Corneat Vision Ltd, Ra'anana (IL)

( * ) Notice: Subject to any disclaimer, the term of this patent is extended or adjusted under 35 U.S.C. 154(b) by 848 days.

(21) Appl. No.: 17/605,030

(22) PCT Filed: Apr. 26, 2020

(86) PCT No.: PCT/IL2020/050470
§ 371 (c)(1),
(2) Date: Oct. 20, 2021

(87) PCT Pub. No.: WO2020/217244
PCT Pub. Date: Oct. 29, 2020

(65) Prior Publication Data
US 2022/0202563 A1 Jun. 30, 2022

Related U.S. Application Data

(60) Provisional application No. 62/838,668, filed on Apr. 25, 2019.

(51) Int. Cl.
*A61F 2/14* (2006.01)
*A61F 2/00* (2006.01)

(52) U.S. Cl.
CPC ............ *A61F 2/1453* (2015.04); *A61F 2/148* (2013.01); *A61F 2002/0081* (2013.01); *A61F 2220/0008* (2013.01); *A61F 2250/0097* (2013.01)

(58) Field of Classification Search
CPC .................... A61F 2/1453; A61F 2/148; A61F 2002/0081; A61F 2220/0008; A61F 2250/0097
(Continued)

(56) References Cited

U.S. PATENT DOCUMENTS 3,737,508 A 5/1973 Weir
3,950,478 A 4/1976 Kenworthy
(Continued)

FOREIGN PATENT DOCUMENTS

CN 108309509 A 7/2018
WO WO-9727824 A1 * 8/1997 ............. A61F 2/142
(Continued)

OTHER PUBLICATIONS

Salvador-Culla, B., & Kolovou, P. E. (2016). Keratoprosthesis: A review of recent advances in the field. Journal of functional biomaterials, 7(2), 13.
(Continued)

*Primary Examiner* — Suba Ganesan
(74) *Attorney, Agent, or Firm* — Mark S. Cohen; PEARL COHEN ZEDEK LATZER BARATZ LLP

(57) ABSTRACT

The invention provides surgical procedures for implanting a keratoprosthesis in an eye of a subject in need using a kit comprising keratoprosthesis comprising a central optical core, a peripheral skirt around said central optical core, comprising at least one biocompatible polymer; and a marking tool comprising a polymeric surface in the shape of said central optical core.

12 Claims, 8 Drawing Sheets

(58) Field of Classification Search
USPC .................................................... 623/5.15
See application file for complete search history.

(56) References Cited

U.S. PATENT DOCUMENTS

| | | | |
|---|---|---|---|
| 3,996,321 | A | 7/1976 | Weinberger |
| 4,189,336 | A | 2/1980 | Hutflesz |
| 4,402,900 | A | 6/1983 | Berry |
| 4,421,707 | A | 12/1983 | Kourtz |
| 4,431,602 | A | 2/1984 | Behrens |
| 4,470,159 | A * | 9/1984 | Peyman .............. A61F 2/16 623/5.11 |
| 4,557,732 | A | 10/1985 | Hahnke |
| 4,643,657 | A | 2/1987 | Achelpohl |
| 4,804,511 | A | 2/1989 | Pieper |
| 5,002,474 | A | 3/1991 | Hoekstra |
| 5,006,123 | A | 9/1991 | Soll |
| 5,122,329 | A | 6/1992 | Mort |
| 5,387,387 | A | 7/1995 | James |
| 5,667,743 | A | 9/1997 | Tai |
| 6,106,552 | A | 8/2000 | Lacombe et al. |
| 6,248,273 | B1 | 6/2001 | Benin |
| 6,252,031 | B1 | 6/2001 | Tsutsumi |
| 11,540,914 | B2 * | 1/2023 | Shiuey .............. A61F 2/1453 |
| 2008/0300680 | A1 * | 12/2008 | Joshua .............. A61F 2/1629 623/6.37 |

FOREIGN PATENT DOCUMENTS

| | | | |
|---|---|---|---|
| WO | WO2002/043622 | A | 6/2002 |
| WO | WO 2002/049535 | | 6/2002 |
| WO | WO 2002/049536 | | 6/2002 |
| WO | WO 2002/049678 | | 6/2002 |
| WO | WO 2002/074189 | | 9/2002 |
| WO | WO 2002/074190 | | 9/2002 |
| WO | WO 2002/074191 | | 9/2002 |
| WO | WO 2005/032400 | | 4/2005 |
| WO | WO 2005/065578 | | 7/2005 |
| WO | WO 2016/199139 | | 12/2016 |
| WO | WO-2019241699 | A1 * | 12/2019 .............. A61B 3/16 |

OTHER PUBLICATIONS

Search Report issued on Sep. 2, 2020 for PCT Application for PCT/IL2020/050470.
IPRP issued on Nov. 4, 2021 for PCT Application No. PCT/IL2020/050470.

* cited by examiner

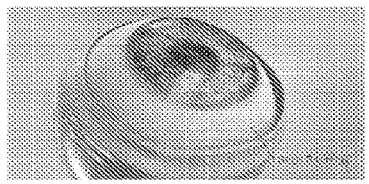
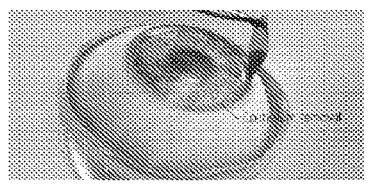
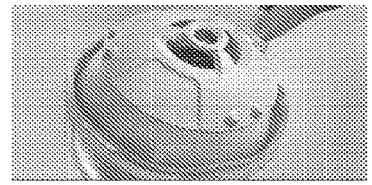
Figure 8A            Figure 8B            Figure 8C
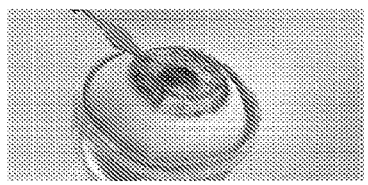
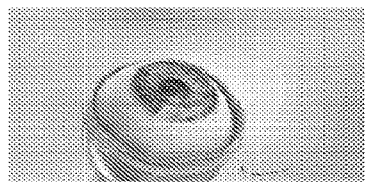
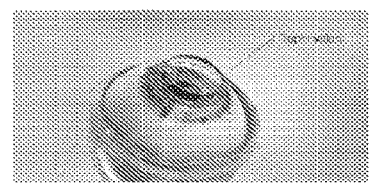
Figure 8D            Figure 8E            Figure 8F
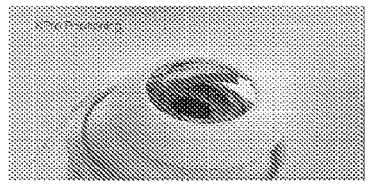
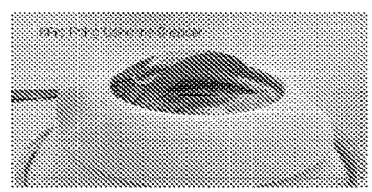
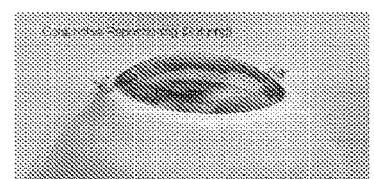
Figure 8G            Figure 8H            Figure 8I
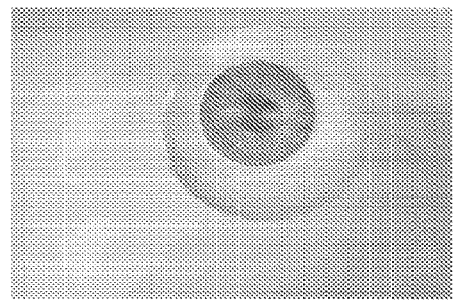
Figure 8J

KERATOPROSTHESIS DEVICES AND KITS AND SURGICAL METHODS OF THEIR USE

CROSS-REFERENCE TO RELATED APPLICATIONS

This application is a National Phase Application of PCT International Application No. PCT/IL2020/050470, International Filing Date Apr. 26, 2020, claiming the benefit of U.S. Patent Application No. 62/838,668, filed Apr. 25, 2019 which is hereby incorporated by reference.

BACKGROUND OF THE INVENTION

Diseases affecting the cornea are a major cause of blindness worldwide, second only to cataract in overall importance. According to the World Health Organization, approximately 2 million new cases are reported each year. Over 50 million people in the world are blind in one or both eyes from corneal injury or disease. Degradation of visual acuity impacts many more.

For various reasons, current solutions for corneal blindness and diseases only address 5%-10% of cases. To date, most patients are treated with Keratoplasty a procedure that relies on transplanting corneal tissue harvested from the deceased. All artificial cornea solutions that are based on implants have failed to address this potential for diversified reasons. Due to risks, complexity, and costs, these are selectively used as a last resort for patients that are not suited for corneal transplant or have failed one. Current solutions for corneal blindness are divided to Keratoplasty (Corneal transplantation) and Keratoprosthesis (Artificial cornea).

During keratoplasty surgery the graft is taken from a recently deceased donor with no known diseases or other factors that may affect the chance of survival of the donated tissue or the health of the recipient. The disadvantage of keratoplasty is a lack of donor tissue, the complexity and costs of operating a cornea bank, and the limited applicability to only some cases. For example, corneal diseases and injuries that leads to vascularization (penetration of blood vessels into the corneal tissue) are not suitable for keratoplasty. Multiple grafting also leads to elevated risk for rejection/failure.

When using an artificial cornea the procedure is known as keratoprosthesis. Traditionally, keratoprosthesis is recommended after a patient has had a failure of one or more donor corneal transplants. While different types of Keratoprosthesis have been approved for limited use by the FDA (see Salvador-Culla et al. *Journal of Functional Biomaterial.* 2016, 7, 13, with a review of recent advances in the field of keratoprosthesis), the only viable solution in the marketplace today is the Boston KPro. Boston KPro is approved by the FDA only for cases that cannot be addressed by Keratoplasty. This is due to many complications and the need for close and lifelong monitoring by an ophthalmologist familiar with the Boston KPro. Life-long topical steroids such as prednisolone acetate is necessary in all KPro eyes to prevent inflammation.

There are multiple disadvantages and failures associated with the known keratoprosthesis options, including diversified postoperative complications which are mainly a result of the device intervention in the physiology of the anterior chamber. Most of the patients (60%-75%) develop glaucoma, elevated intraocular pressure, which can lead to blindness, limited field of vision and cataract. Furthermore, there is poor biointegration of the known keratoprosthesis that necessitates daily antibiotic drops, lifelong treatment with topical steroids, and intensive lifelong ophthalmologist follow up.

After the implantation of known keratoprosthesis the access to the internal parts of the eye for performing surgical procedures such as cataract and retinal surgery is very limited at best. Due to this, the primary keratoprosthesis surgery is often combined with other procedures including implantation of glaucoma filtration devices, and a cataract surgery (replacing the lens with synthetic Intra Ocular Lens) making the procedure longer, more dangerous and costly.

WO 2016/199139 disclosed a keratoprosthesis assembly comprising a central optical core; and a peripheral skirt comprising at least one porous biocompatible layer and methods of using it in keratoprosthesis procedures.

SUMMARY OF THE INVENTION

The present invention provides a keratoprosthesis comprising: (a) a central optical core comprising a central optical lens having an anterior surface and a posterior surface; and (b) a peripheral skirt around said central optical core, comprising at least one biocompatible polymer and having a width capable of being placed under the conjunctiva and above sclera of the eye; wherein said central optical core comprises an anterior rim extending radially (i.e. around, surrounding) from the anterior surface; and a posterior rim extending radially (i.e. around, surrounding) from and below the posterior surface; wherein said anterior rim comprises at least two suturing holes and at least two access ports; and wherein said posterior rim comprises at least two extended flanges.

The term "keratoprosthesis" should be understood to encompass an artificial cornea used in the keratoprothesis procedure when replacing a diseased cornea of a subject in need thereof. The terms "keratoprosthesis assembly", "artificial cornea" and "artificial cornea assembly" are used herein interchangeably. Thus, the artificial cornea of the invention comprises a central optical core which is used, among other uses, to cover the anterior chamber of the eye, located at the center of the artificial cornea of the invention and a peripheral skirt located around said optical core traversing the anterior sclera beneath the conjunctiva-tenon complex.

The term "central optical core" of an artificial cornea of the invention (keratoprosthesis of the invention) provides the center part of the assembly which includes a central optical lens of the keratoprosthesis covering the anterior chamber of the eye (after trephination of the diseased cornea). Said central optical lens has an anterior surface (surface forming the top upper part of the lens) and a posterior surface (surface forming the bottom part of the lens).

In some embodiments, the optical lens is formed from flexible polymer(s). In other embodiments, the optical lens is formed from rigid polymer(s). In some embodiments, the optical lens is made from an acrylic, clear polymer, with varying dioptric power in accordance with the need of the subject.

In some embodiments, said central optical lens is formed from acrylic, silicate or other clear, durable polymer and any combinations thereof.

The optical lens optionally further comprises an external layer repelling depositions. This external layer can be formed from a silicone hydrogel similar to contact lenses.

In some embodiments, said optical lens has a diameter ranging from about 3 to about 15 mm. In other embodiments, said central optical lens has a diameter of at least 3 mm. In other embodiments, said central optical lens has a diameter of at least 5 mm. In other embodiments, said central optical lens has a diameter of at least 7 mm. In other embodiments, said central optical lens has a diameter in the range of about 3 to about 6 mm. In further embodiments, said central optical lens has a diameter in the range of between 6 to 14 mm.

In further embodiments, said central optical lens has a thickness ranging from about 500 micrometers to 3000 micrometers. In other embodiments said central optical lens has a thickness ranging from about 500 micrometers to 2500 micrometers. In further embodiments said central optical lens has a thickness ranging from about 500 micrometers to 1500 micrometers.

In other embodiments, said central optical lens has a diopter ranging from about 10 to about 70 diopters.

The optical core of the keratoprosthesis of the invention further comprises an anterior rim extending radially from the anterior surface of the optical lens and going around the optical lens, and a posterior rim extending radially down/below from the posterior surface of the optical lens and around the optical lens.

The anterior rim comprises at least two suturing holes (i.e. apertures in rim width that are used for suturing the keratoprosthesis of the invention into the subject eye with a surgical suturing thread) and at least two access ports (i.e. carved out holes or arches in the width of the rim used, for example, during the surgical implantation procedure to access the parts of the eye that are being treated beneath the keratoprosthesis of the invention. The access ports also allow for post-operative procedures to be done in the eye of the subject, after the implantation of the keratoprosthesis of the invention).

In some embodiments, said anterior rim comprises a proximal zone extending radially from the anterior surface of the optical lens and going around the optical lens, said proximal zone is formed from a transparent/clear material (for example the material of the optical les it is surrounding) and is coherent and homogeneous and a distal zone extending from and around the proximal zone comprising said at least two suturing holes and at least two access ports. The transparent/clear proximal zone of the anterior rim provides aid to the surgeon while transplanting the keratoprosthesis of the invention, so that said surgeon can properly place the keratoprosthesis of the invention at the appropriate position in the trephined cornea. Furthermore, as this part of the keratoprosthesis of the invention is visible when device is transplanted, this provides an aesthetic feature making the eye having the transplant being visibly similar to a healthy normal eye. In some further embodiments said distal zone is formed from similar material as the proximal zone. In other embodiments said distal zone is formed from different materials as the proximal zone. In some embodiments, said anterior rim comprises at least three suturing holes. In other embodiments, said anterior rim comprises at least four suturing holes. In other embodiments, said anterior rim comprises at least six suturing holes. In further embodiments, said anterior rim comprises at least two pairs of suturing holes. In further embodiments, said anterior rim comprises at least three pairs of suturing holes.

In some embodiments, said suturing holes are located at predetermined distance from each other on the anterior rim. In some embodiments, said pairs of suturing holes are located at predetermined distance from each other on the anterior rim.

In some embodiments, said anterior rim comprises at least three access ports. In some embodiments, said anterior rim comprises at least four access ports. In some embodiments, said anterior rim comprises at least six access ports. In some embodiments, said anterior rim comprises 3, 4, 5, 6, 7, 8, 9, 10 or 15 access ports.

In further embodiments, said access ports are located at predetermined distances from each other on the anterior rim.

In some embodiments, said anterior rim further comprises at least one biocompatible polymer. Said biocompatible polymer located on the anterior rim (in some embodiments in apertures formed on the rim) allow for bio-assimilation of the anterior rim with the tissue of the eye.

In some embodiments, said anterior rim has a width of at least 1 mm. In some embodiments, said anterior rim has a width of at least 2 mm. In some embodiments, said anterior rim has a width of at least 3 mm. In some embodiments, said anterior rim has a width of at least 5 mm. When referring to anterior rim's width it should be understood to relate to the distance between the point of contact of said rim with said anterior surface and its furthest point following the curvature of said rim.

The posterior rim is extended radially from and below the surface of the lens and comprises at least two extended flanges each one extending down from the width of the rim. The posterior rim allows for said central optical core to be placed into a trephined cornea of the subject in need thereof so to traverse the width of the recipient cornea. Said at least two flanges extending down from the width of the rim secure the holding of the keratoprosthesis of the invention into the trephined cornea so that it will not move, be thrusted out or pushed out of the trephined cornea during or after the procedure. In some embodiments, said posterior rim comprises at least three extended flanges. In some embodiments, said posterior rim comprises at least four extended flanges. In some embodiments, said posterior rim comprises at least five extended flanges. In some embodiments, said posterior rim comprises at least six extended flanges. In some embodiments, said posterior rim comprises 2, 3, 4, 5, 6, 7, 8, 9, 10 or 15 extended flanges.

In some embodiments, said extended flanges are located at predetermined distances from each other on the posterior rim.

In other embodiments, said posterior rim has a width (i.e. the part that radially extends from the surface of the lens forming a radial rim extending below the surface of the lens excluding said flanges) of at least 1 mm. In other embodiments, said posterior rim has a width of at least 2 mm. In other embodiments, said posterior rim has a width of at least 3 mm. In other embodiments, said posterior rim has a width of at least 4 mm. In other embodiments, said posterior rim has a width of at least 5 mm. In other embodiments, said posterior rim has a width of at least 6 mm. In other embodiments, said posterior rim has a width of at least 7 mm. In other embodiments, said posterior rim has a width of at least 8 mm. In other embodiments, said posterior rim has a width of at least 9 mm. In other embodiments, said posterior rim has a width of 1, 2, 3, 4, 5, 6, 7, 8, 9 mm. When referring to posterior rim's width it should be understood to relate to the distance between the point of contact of said rim with said posterior surface and its furthest point following the curvature of said rim.

In some embodiments, said anterior rim is formed from the same material as at least one of the optical lens and the posterior rim. In other embodiments, said posterior rim is formed of the same material as at least one of the optical lens and the anterior rim. In some other embodiments, said elements of the optical core, i.e. the optical lens, the anterior rim and the posterior rim are all made of the same material. In some other embodiments, said elements of the optical core, i.e. the optical lens, the anterior rim and the posterior rim are all made of different materials.

The term "peripheral skirt" should be understood to encompass the part of the keratoprosthesis of the invention that surrounds radially substantially all the perimeter of the central optical core of the keratoprosthesis assembly of the invention, extending from the anterior surface of the optical lens. Said skirt comprises at least one biocompatible layer as defined herein above and below.

In some embodiments, said peripheral skirt is extended towards the conjunctiva of the eye. In further embodiments, said peripheral skirt is formed in a manner that enables placing it under the conjunctiva of the eye. Placing of the skirt beneath the conjunctiva is performed after dissecting the conjunctiva from its limbal anchorage (this procedure is termed peritomy) and elevating it so to create a space to accommodate the said skirt.

In some embodiments, said peripheral skirt has a width of at least 3 mm. In other embodiments, said peripheral skirt has a width of between 3 to 9 mm. In further embodiments, said peripheral skirt has a width ranging from about 4 to about 6 mm.

In some embodiments, said peripheral skirt has a thickness ranging from about 100 to about 2000 micron.

In some embodiments, said at least one biocompatible polymer of said peripheral skirt is at least one porous biocompatible polymer.

In some embodiments, said at least one porous biocompatible polymer of said peripheral skirt has pores of at least 0.1 µm. In some embodiments, said at least one porous biocompatible polymer of said peripheral skirt has pores of between about 0.1 to 10 µm. In some embodiments, said at least one porous biocompatible polymer of said peripheral skirt has pores of about 0.1, 0.2, 0.3, 0.4, 0.5, 0.6, 0.7, 0.8. 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 µm. In some embodiments further pores are formed on the outer surface of said peripheral skirt, said further pores of between about 0.1 to 10 µm. In some embodiments further pores are formed on the outer surface of said peripheral skirt, said further pores of about 0.1, 0.2, 0.3, 0.4, 0.5, 0.6, 0.7, 0.8. 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 µm. In some embodiments, said further pores have predetermined design patterns.

In further embodiments, said at least one biocompatible polymer of said peripheral skirt is a nonwoven fabric.

In further embodiments, said biocompatible polymer of said peripheral skirt comprises nanofibers. In some embodiments, said nanofibers have a diameter of between about 200 nm to 4 µm. In some embodiments, said nanofibers have a diameter of between about 500 nm to 2 µm.

In some embodiments, said at least one biocompatible polymer of said peripheral skirt is formed by at least one process selected from drawing, electrospinning, self-assembly, template synthesis, and thermal-induced phase separation and any combinations thereof. In some embodiments, said at least one biocompatible polymer of said peripheral skirt is formed by electrospinning process.

In further embodiments, said at least one biocompatible polymer of said peripheral skirt is selected from poly(DTE carbonate) polycaprolactone (PCL), polylactic acid (PLA), polyurethane, polycarbonate, poly-L-lactic acid (PLLA), Poly(DL-lactide-co-caprolactone, Poly(ethylene-co-vinyl acetate) vinyl acetate, Poly(methyl methacrylate), Poly(propylene carbonate), Poly(vinylidene fluoride), Polyacrylonitrile, Polycaprolactone, Polycarbomethylsilane, Polylactic acid, Polystyrene, Polyvinylpyrrolidone, poly vinyl alcohol (PVA), polyethylene oxide (PEO), polyvinyl chloride (PVC), hyaluronic acid (HA), chitosan, alginate, polyhydroxybuyrate and its copolymers, Nylon 11, Cellulose acetate, hydroxyappetite, poly(3-hydroxybutyric acid-co-3-hydroxyvaleric acid), poly(DL-lactide), polycaprolactone, and poly(L-lactide) or any combination thereof.

The term "porous biocompatible layer" should be understood to encompass any type of layer (or film) formed from material that has the ability to perform its desired function with respect to a medical therapy (i.e. keratoprosthesis), without eliciting any undesirable local or systemic effects in the recipient or beneficiary of that therapy, but generating the most appropriate beneficial cellular or tissue response in that specific situation, and optimizing the clinically relevant performance of that therapy. The biocompatible layer of the skirt of the assembly of the invention allows the implanted artificial cornea to exist in harmony with tissue it is in contact with without causing deleterious changes. The layer is porous, having pore size of at least at least about 0.1 µm (when referring to pore size it should be understood to relate to the average pore sizes).

In some embodiments, said porous biocompatible layer is a fibrous porous biocompatible layer (i.e. the layer or film is formed of fibers), having pore size of at least about 2 µm.

In some embodiments, at least one porous biocompatible layer has pores of between about 2 µm to about 100 µm in width.

In other embodiments, said at least one porous biocompatible layer is a polymeric layer. Thus, under this embodiment, the layer or film of the skirt is made of at least one polymer material.

In other embodiments, said at least one porous biocompatible layer is a nonwoven fabric. Thus, under this embodiment, said layer or film of the skirt is a fabric-like material made from long fibers, bonded together by chemical, mechanical, heat or solvent treatment.

In further embodiments, said porous biocompatible layer comprises nanofibers. Thus, under this embodiment, the skirt is formed of fibers with diameters of less than 2000 nanometres. In some embodiments, nanofibers are produced by any type of process including, but not limited to melt processing, interfacial polymerization, electrospinning, antisolvent-induced polymer precipitation, electrostatic spinning, catalytic synthesis and any combinations thereof.

In further embodiments, said at least one porous biocompatible layer comprises poly(DTE carbonate) polycaprolactone (PCL), polylactic acid (PLA), polyurethane, polycarbonate, poly-L-lactic acid (PLLA), Poly(DL-lactide-co-caprolactone, Poly(ethylene-co-vinyl acetate) vinyl acetate, Poly(methyl methacrylate), Poly(propylene carbonate), Poly(vinylidene fluoride), Polyacrylonitrile, Polycaprolactone, Polycarbomethylsilane, Polylactic acid, Polystyrene, Polyvinylpyrrolidone, poly vinyl alcohol (PVA), polyethylene oxide (PEO), polyvinyl chloride (PVC), hyaluronic acid (HA), chitosan, alginate, polyhydroxybuyrate and its copolymers, Nylon 11, Cellulose acetate, hydroxyappetite, poly(3-hydroxybutyric acid-co-3-hydroxyvaleric acid), poly(DL-lactide), polycaprolactone, and poly(L-lactide) or any combination thereof.

In some further embodiments, said porous biocompatible layer comprises electrospun nanofibers. In another embodiment, said at least one porous biocompatible layer is formed by electrospinning process.

The term "electrospinning" or "electrospun" or any of its lingual deviations should be understood to encompass a process using an electrical charge to draw very fine (typically in the micro or nano scale) fibers from a liquid. Electrospinning from molten precursors is also practiced; this method ensures that no solvent can be carried over into the final product. The fibers produced using electrospinning processes have increased surface area to volume ratio. Various factors are known to affect electrospun fibers include, but are not limited to solution viscosity, surface tension, electric field intensity and distance.

In a typical electrospinning process a sufficiently high voltage is applied to a liquid droplet of a polymeric material (a polymer solution, a monomeric precursor thereof, sol-gel precursor, particulate suspension or melt), the body of the liquid becomes charged, and electrostatic repulsion counteracts the surface tension and droplet is stretched, at a critical point a stream of liquid erupts from the surface. If the molecular cohesion of the liquid is sufficiently high, stream breakup does not occur (if it does, droplets are electrosprayed) and a charged liquid jet is formed. As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector. The elongation and thinning of the fiber that results from this bending instability leads to the formation of uniform fibers with nanometer-scale diameters.

Biocompatible polymers which may be applied in an electrospinning process include but are not limited to poly (DTE carbonate) polycaprolactone (PCL), polylactic acid (PLA), polyurethane, polycarbonate, poly-L-lactic acid (PLLA), Poly(DL-lactide-co-caprolactone, Poly(ethylene-co-vinyl acetate) vinyl acetate, Poly(methyl methacrylate), Poly(propylene carbonate), Poly(vinylidene fluoride), Polyacrylonitrile, Polycaprolactone, Polycarbomethylsilane, Polylactic acid, Polystyrene, Polyvinylpyrrolidone, poly vinyl alcohol (PVA), polyethylene oxide (PEO), polyvinyl chloride (PVC), hyaluronic acid (HA), chitosan, alginate, polyhydroxybuyrate and its copolymers, Nylon 11, Cellulose acetate, hydroxyappetite, or any combination thereof. Biodegradable and biocompatible polymers include but are not limited to poly(3-hydroxybutyric acid-co-3-hydroxyvaleric acid), poly(DL-lactide), poly urethane, polycaprolactone, and poly(L-lactide) or any combination thereof.

Electrospun fibers are typically several orders in magnitude smaller than those produced using conventional spinning techniques. By optimizing parameters such as: i) the intrinsic properties of the solution including the polarity and surface tension of the solvent, the molecular weight and conformation of the polymer chain, and the viscosity, elasticity, and electrical conductivity of the solution; and the operational conditions such as the strength of electric field, the distance between spinneret and collector, and the feeding rate of the solution, electrospinning is capable of generating fibers as thin as tens of nanometers in diameter. Additional parameters that affect the properties of electrospun fiber include the molecular weight, molecular-weight distribution and structure (branched, linear etc.) of the polymer, solution properties (viscosity, conductivity and surface tension), electric potential, flow rate and concentration, distance between the capillary and collection screen, ambient parameters (temperature, humidity and air velocity in the chamber), motion of target screen (collector) and so forth. Fabrication of highly porous fibers may be achieved by electrospinning the jet directly into a cryogenic liquid. Well-defined pores developed on the surface of each fiber as a result of temperature-induced phase separation between the polymer and the solvent and the evaporation of solvent under a freeze-drying condition.

Several approaches have been developed to organize electrospun fibers into aligned arrays. For example, electrospun fibers can be aligned into a uniaxial array by replacing the single-piece collector with a pair of conductive substrates separated by a void gap. In this case, the nanofibers tend to be stretched across the gap oriented perpendicular to the edges of the electrodes. It was also shown that the paired electrodes could be patterned on an insulating substrate such as quartz or polystyrene so the uniaxially aligned fibers could be stacked layer-by-layer into a 3D lattice. By controlling the electrode pattern and/or the sequence for applying high voltage, it is also possible to generate more complex architectures consisting of well-aligned nanofibers.

Electrospun nanofibers could also be directly deposited on various objects to obtain nanofiber-based constructs with well-defined and controllable shapes. In addition, one can manually process membranes of aligned or randomly oriented nanofibers into various types of constructs after electrospinning: for example, fabrication of a tube by rolling up a fibrous membrane or the preparation of discs with controllable diameters by punching a fibrous membrane.

The present invention relates to any eletrospinning technique known in the art, which includes *Electrospinning*, J. Stanger, N. Tucker, and M. Staiger, I-Smithers Rapra publishing (UK), *An Introduction to Electrospinning and Nanofibers*, S. Ramakrishna, K. Fujihara, W-E Teo, World Scientific Publishing Co. Pte Ltd (June 2005), *Electrospinning of micro- and nanofibers: fundamentals and applications in separation and filtration processes*, Y. Fillatov, A. Budyka, and V. Kirichenko (Trans. D. Letterman), Begell House Inc., New York, USA, 2007, which are all incorporated herein by reference in their entirety.

Suitable electrospinning techniques are disclosed, e.g., in International Patent Application, Publication Nos. WO 2002/049535, WO 2002/049536, WO 2002/049536, WO 2002/049678, WO 2002/074189, WO 2002/074190, WO 2002/074191, WO 2005/032400 and WO 2005/065578, the contents of which are hereby incorporated by reference. It is to be understood that although the according to the presently preferred embodiment of the invention is described with a particular emphasis to the electrospinning technique, it is not intended to limit the scope of the invention to the electrospinning technique. Representative examples of other spinning techniques suitable for the present embodiments include, without limitation, a wet spinning technique, a dry spinning technique, a gel spinning technique, a dispersion spinning technique, a reaction spinning technique or a tack spinning technique. Such and other spinning techniques are known in the art and disclosed, e.g., in U.S. Pat. Nos. 3,737,508, 3,950,478, 3,996,321, 4,189,336, 4,402,900, 4,421,707, 4,431,602, 4,557,732, 4,643,657, 4,804,511, 5,002,474, 5,122,329, 5,387,387, 5,667,743, 6,248,273 and 6,252,031 the contents of which are hereby incorporated by reference.

In some embodiments, the keratoprosthesis of the invention further comprising at least one pharmaceutically active agent.

In other embodiments, said at least one pharmaceutically active agent is incorporated into at least one of: the peripheral skirt, the anterior rim, the posterior rim and any combinations thereof.

In some embodiments, said at least one pharmaceutically active agent is selected from an antibiotic agent, a protein, type I collagen, fibronectin, or TGF-beta 2, heparin, growth factors, antibodies, antimetabolites, chemotherapeutic agents, and any combinations thereof.

In some embodiments, said optical core and peripheral skirt are mechanically attached to each other (using for example mechanical means for attaching the core to the skirt, such as for example a strip of layer connecting them or a suture). In other embodiments, said optical core and peripheral skirt are chemically attached to each other (using for example any gluing or connecting component, fusing them together using heat or pressure and so forth).

The invention further provides a kit comprising: a keratoprosthesis comprising: (a) a central optical core comprising a central optical lens having an anterior surface and a posterior surface; and (b) a peripheral skirt around said central optical core, comprising at least one biocompatible polymer and having a width capable of being placed under the conjunctiva and above sclera of the eye; wherein said central optical core comprises an anterior rim extending radially from the anterior surface and a posterior rim extending radially from and below the posterior surface; wherein said anterior rim comprises at least two suturing holes and at least two access ports; and wherein said posterior rim comprises at least two extended flanges; and a marking tool comprising a polymeric surface in the shape of said central optical core, having bumps protruding below the polymeric surface, located at the positions of said at least two suturing holes, at least two access ports of the central optical core and the trephination edge. In some embodiments, said kit of the invention further comprising ophthalmological ink deposited on the bumps protruding below the polymeric surface as described above. In other embodiments, said kit of the invention further comprises a snapping tool having an elongated rod portion, wherein its end part is angled. Said snapping tool allows for the surgeon performing the surgical procedure to locate and fit the keratoprosthesis of the invention into the trephined cornea of the subject. In some embodiments, a kit of the invention further comprises instructions for use in a surgical procedure for implanting a keratoprosthesis in a subject.

After the trephination of the diseased part of the cornea is removed, and since the optical core is transparent, the marking tool used in a kit of the invention allows the surgeon that performs the surgical procedure to know exactly where the suturing holes are located on the ocular surface, so that it will be very easy to insert the suturing thread at the exact places where the suturing holes of the keratoprosthesis of the invention that is implanted are located. Furthermore, the marking of the accesses ports allows the surgeon performing the surgical procedure to know and see clearly where it is possible to access the anterior chamber of the eye under the keratoprosthesis of the invention to be implanted without causing any rupture of trauma to the eye or the assembly. The marking of the trephined edge allows the surgeon to place the trephination tool exactly at the position and size of the optical central core of the keratoprosthesis of the invention, so that the fit of the assembly of the invention is exact.

The invention further provides a surgical procedure for implanting a keratoprosthesis in a subject in need there of comprising the steps of: (1) Providing a kit as disclosed herein; (2) performing a 360 degree peritomy in the eye of said subject; (3) performing epithelial debridement; (3) marking the center of the cornea with a surgical marker; (4) marking the suturing and access ports on the eye of the subject using the marking tool of the kit using the mark of the center of the cornea for reference; (5) pre-placing of corneal anchoring suture threads in the marked suturing holes; (6) intra-cameral (in the anterior eye) injection of anesthetic agent and/or epinephrine and/or (OVD) ophthalmic viscosurgical device (this secures the eye form once opened thus creating a safe, closed chamber, during the entire procedure); (7) trephination and removal of central diseased cornea; (8) approximation of keratoprosthesis of the invention by tying of sutures made in the eye with the suturing holes in the keratoprosthesis of the invention (this allows for keratoprosthesis fitting onto the ocular surface); (9) OVD exchange with balanced salt solution (BSS) (thus refilling the anterior eye with physiologic liquid); (10) tying closure of conjunctiva over the keratoprosthesis skirt and rim with sutures (degradable) and optionally with fibrin placement sub-conjunctivally. This step seals the eye and ocular surface at the completion of the procedure.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 8A-8J shows a cornea implantation surgical procedure of the invention using a keratoprosthesis and kit of the invention.

Figure 1:
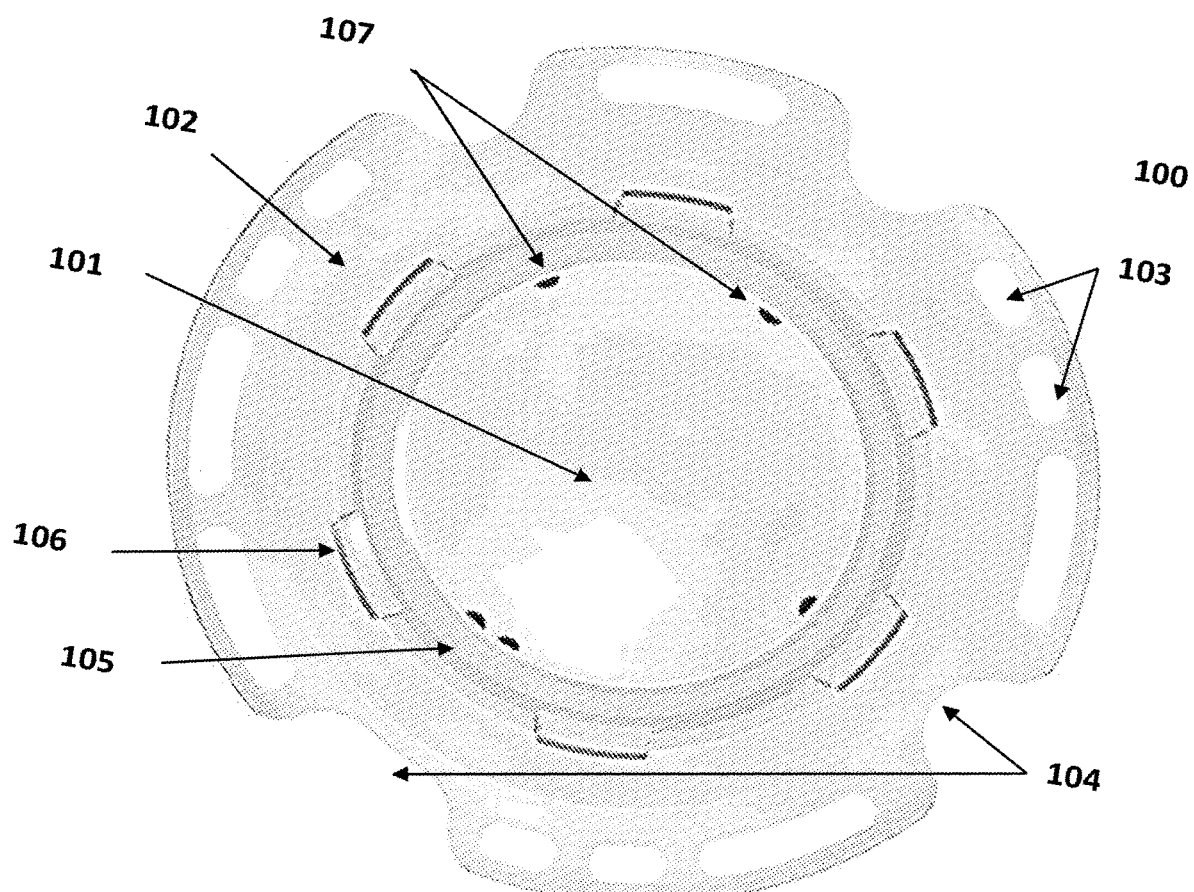
FIG. 1 shows the central optical core of a keratoprosthesis of the invention from a bottom view (the open posterior part of the device).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

FIG. 1 shows a bottom view (a view from the posterior open part of the device of the invention) the optical central core of a keratoprosthesis of the invention (100), showing the optical lens (101), the anterior rim (102) extending around from said optical lens (from its anterior surface). The anterior rim is showing the suturing holes (103) and the access ports (104). Further the posterior rim is shown (105) extending below and around the optical lens (from its posterior surface) and the flanges (106) extending from said posterior rim. The figure also shows the marking of the access ports (107).

Figure 2:
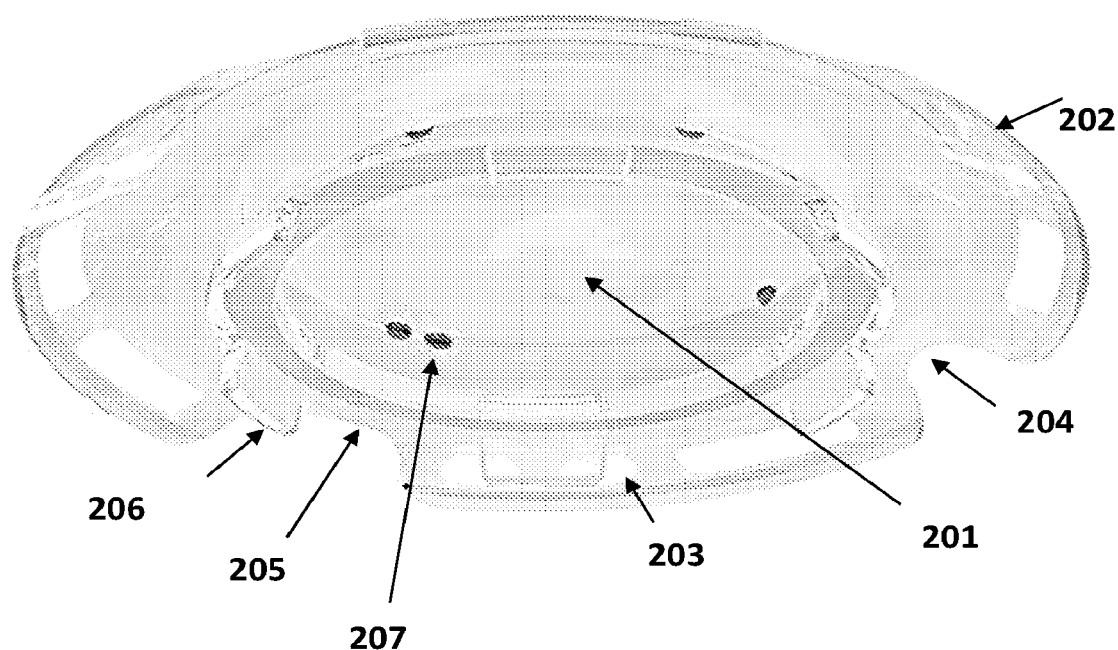
FIG. 2 shows the central optical core of a keratoprosthesis of the invention from a bottom view (the open posterior part of the device).

FIG. 2 shows a bottom side view (a view from the posterior open part of the device of the invention) the optical central core of a keratoprosthesis of the invention (200), showing the optical lens (201), the anterior rim (202) extending around from said optical lens (from its anterior surface). The anterior rim is showing the suturing holes (203) and the access ports (204). Further the posterior rim is shown (205) extending below and around the optical lens (from its posterior surface) and the flanges (206) extending from said posterior rim. The figure also shows the marking of the access ports (207).

Figure 3:
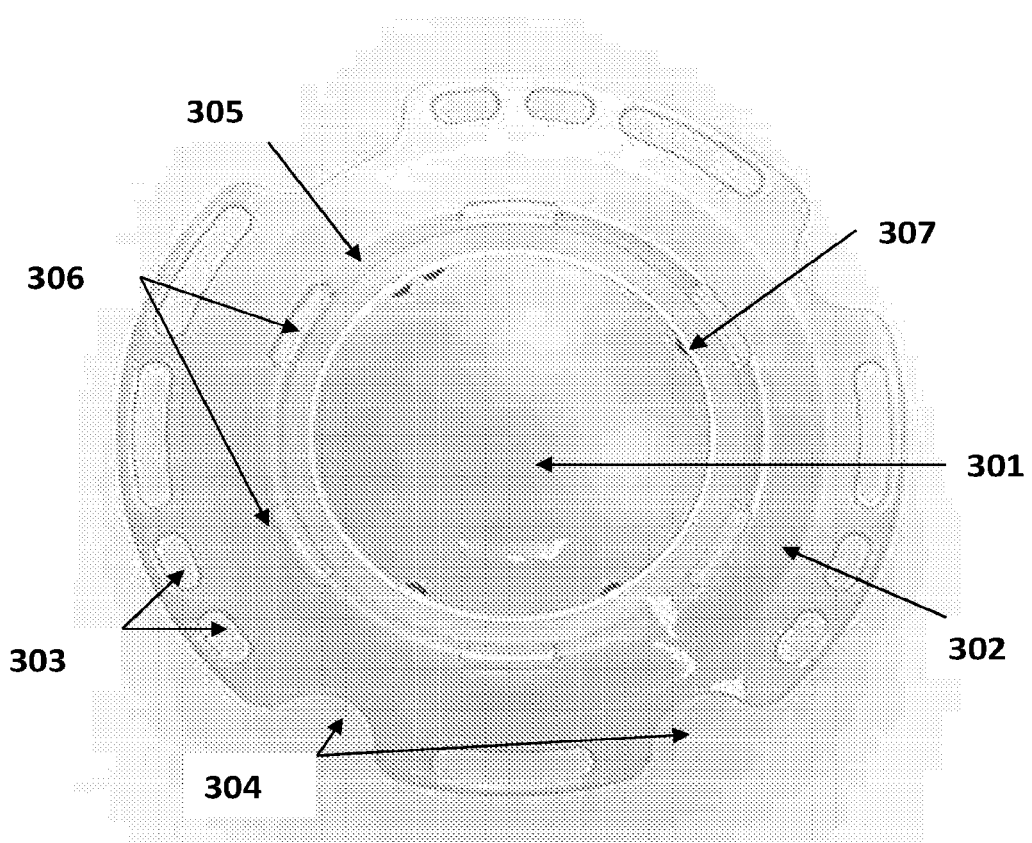
FIG. 3 shows the central optical core of a keratoprosthesis of the invention from a top view (the anterior part of the device).

FIG. 3 shows a top view (a view from the anterior side of the device of the invention) the optical central core of a keratoprosthesis of the invention (300), showing the optical lens (301), the anterior rim (302) extending around from said optical lens (from its anterior surface). The anterior rim is showing the suturing holes (303) and the access ports (304). Further the posterior rim is shown (305) extending below and around the optical lens (from its posterior surface) and the flanges (306) extending from said posterior rim. The figure also shows the marking of the access ports (307).

Figure 4:
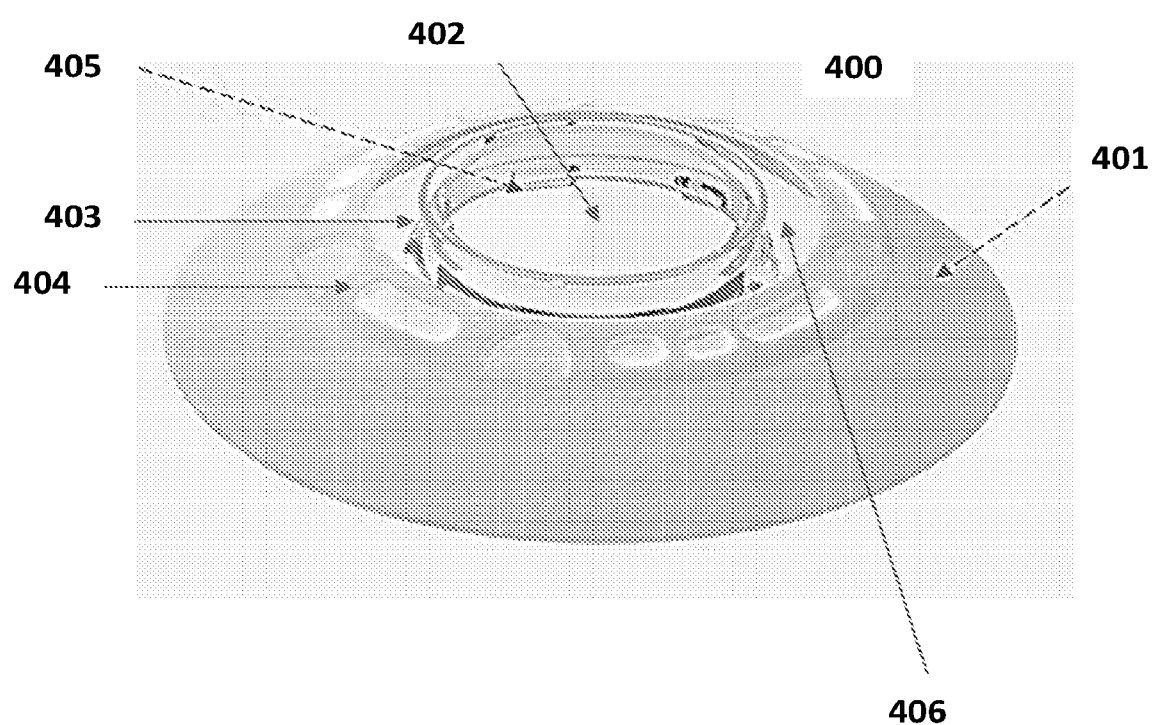
FIG. 4 shows a keratoprosthesis of the invention.

FIG. 4 shows a keratoprosthesis of the invention (400), showing the peripheral skirt (401) around said central optical core (placed on the distal zone of the anterior rim). The figure also shows the optical lens (402), from which the posterior rim (403) extends around and below its posterior surface. Said posterior rim shows the flanges (405). The figure also shows the proximal zone (406) of the anterior rim extending around and from the optical lens (402) and the distal zone (404).

Figure 5A:
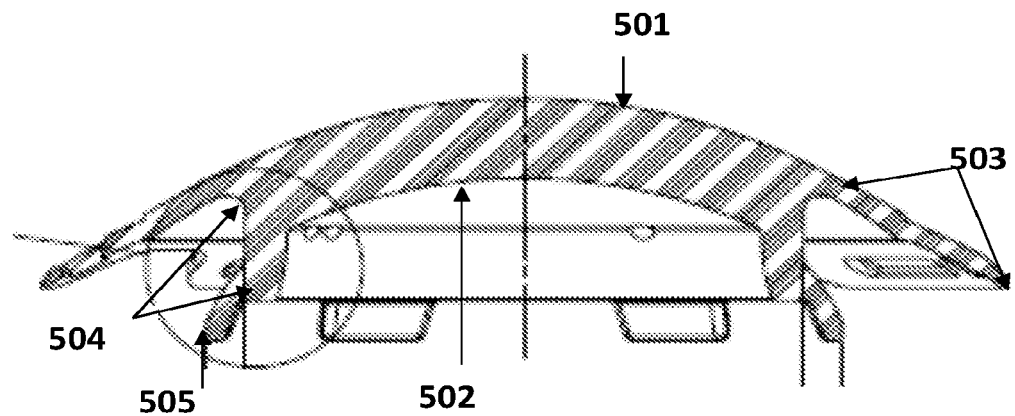
FIG. 5A-5B shows a cross section of the central optical core of a keratoprosthesis of the invention (5A) and a detail thereof (5B).

FIG. 5A shows a cross section of the central optical core of a keratoprosthesis of the invention (500) showing the anterior surface of the optical lens (501) and the posterior surface of the optical lens (502). The figure shows in cross section the width of the anterior rim (503) extending from the anterior surface of the optical lens, the width of the posterior rim (504) extending below the posterior surface of the optical lens and the flanges (505). The space formed between the anterior rim and the posterior rim is able to accommodate the edges of the trephined cornea and thus holding the device on the eye of the subject firmly in position, the suturing reinforces the stability of the device in the eye.

Figure 5B:
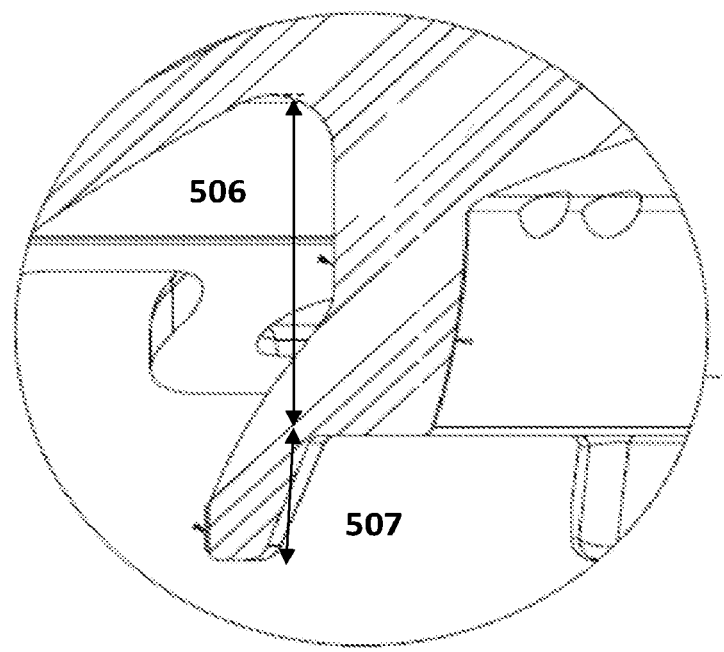

FIG. 5B shows a detail of the cross section of the central optical core of a keratoprosthesis of the invention of FIG. 5A, showing the posterior rim width (506) and the flange (507).

Example 1: In Vivo Examination in NZW Rabbits of a Keratoprosthesis of the Invention Keratoprosthesis of the invention were implanted in 8 rabbits unilaterally and followed up for 6 months. Upon completion, progressive integration with no inflammatory rejections were recorded.

Methods: Eight male NZW rabbits were subjected to a unilateral intraocular implantation of the keratoprosthesis of the invention, while the contralateral eye serves as an untreated control, all under Good Laboratory Practice guidelines. Eight animals were clinically observed for a duration of 6-months to assess safety, during which the eyes are repeatedly monitored by slit-lamp bio-microscopy. At termination, eyes will be enucleated and evaluated histologically.

Figure 6:
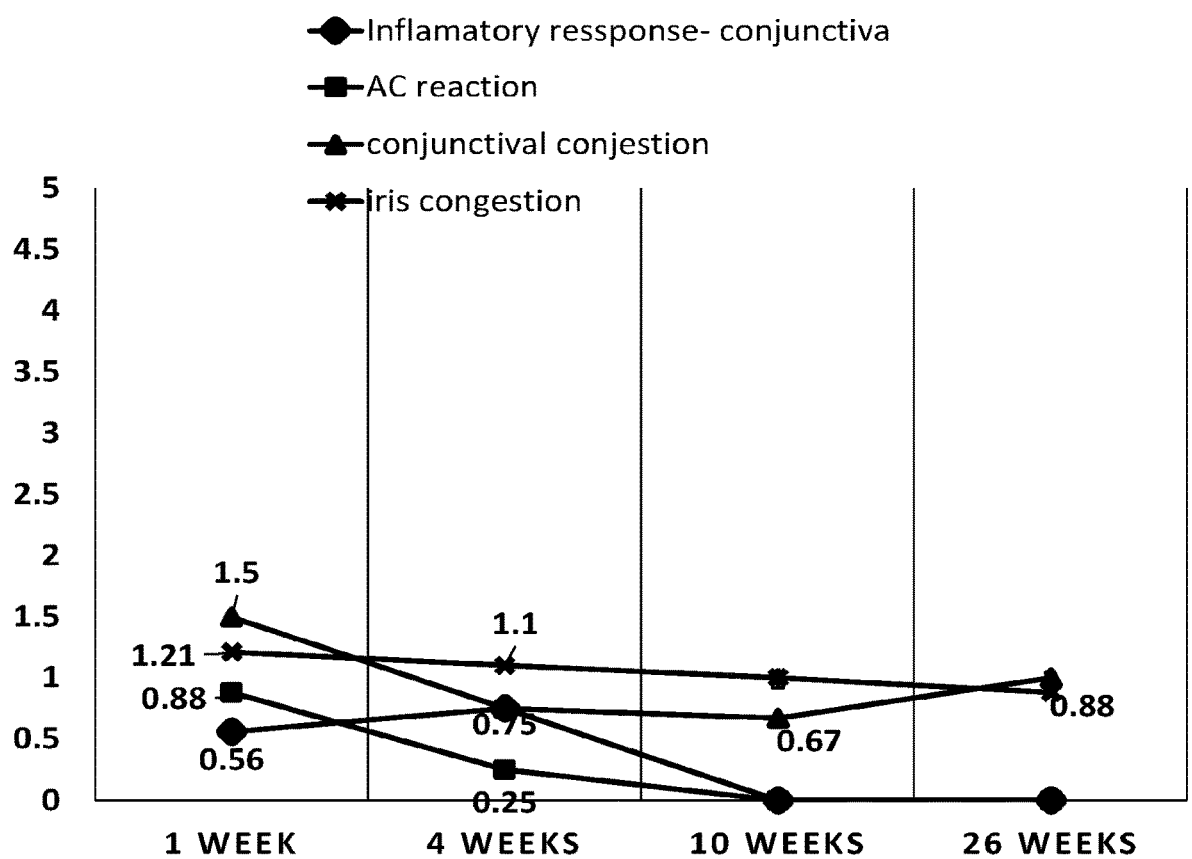
FIG. 6 shows the results of the clinical evaluation of an implanted keratoprosthesis of the invention in a NZW rabbit during 26 weeks from implantation.
Figure 7A:
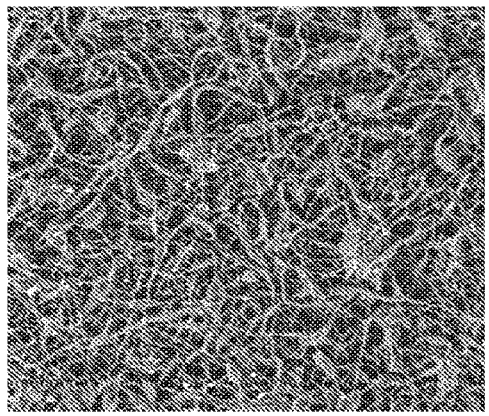
FIG. 7A-7D show tissue processing and histology of the NSW rabbit implanted with a keratoprosthesis of the invention. Eyes implanted were embedded in SPURR blocks. Each block was bisected sagittally through the center of the eye and stained with hematoxylin and eosin (H&E) and Masson's Trichrome (MT).
Figure 7B:
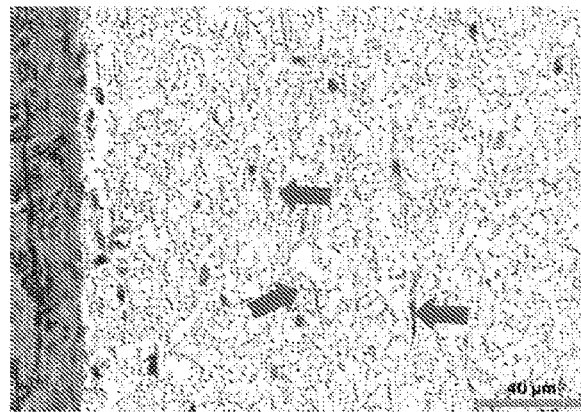
Figure 7C:
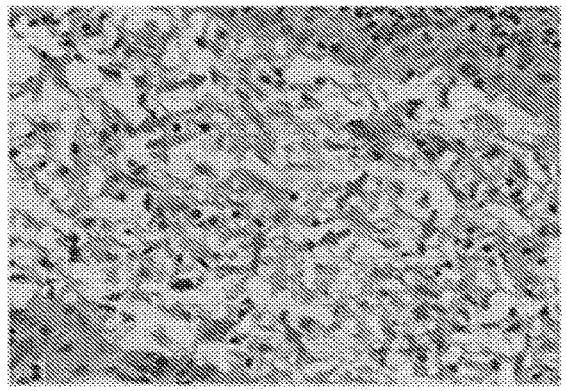
Figure 7D:
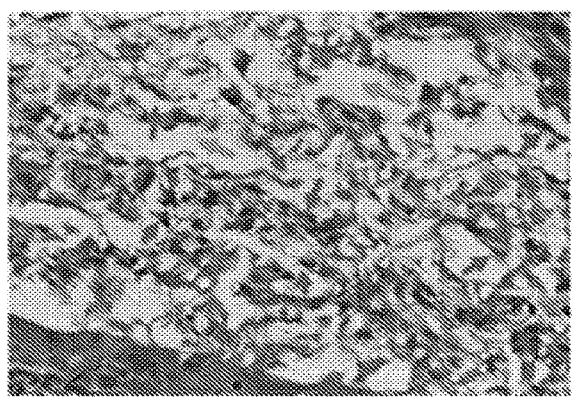

Results: Clinical evidence shows progressive integration and cessation of inflammatory response. Eyes are all intact with no evident breach of integrity or leak of aqueous humor. Animals exhibit use of implanted eyes routinely. Some animals exhibit iatrogenic (surgically induced) Cataract. FIG. 6 shows the results of the clinical evaluation of an implanted keratoprosthesis of the invention in a NZW rabbit during 26 weeks from implantation in terms of inflammatory response of the conjunctiva, anterior chamber (AC) reaction, conjunctiva and iris congestion. Histological data and slides prove seamless and durable tissue integration of the deice with the ocular wall (FIGS. 7A-7D). Clinical and histopathological findings of low and gradually decreasing inflammatory reaction coupled with progressive integration of the peripheral skirt prove short and medium-term safety.

The surgical procedure using a kit and keratoprosthesis of the invention are shown in FIGS. 8A-8J. In FIG. 8A a peritomy of 360 degrees is made, elevating both conjunctiva and tenon; FIG. 8B shows the removal of epithelial cells layer. FIG. 8C shows the marking of the native cornea's center and suturing holes with the dedicated marker tool. FIG. 8D shows the creation of two ports to the anterior chamber for infusion and tools after which the eye is filled with viscoelastic material; FIG. 8E shows the anchoring sutures—three limbal sutures are pre-placed for optic anchoring at 120 degrees apart as marked by the marker; FIG. 8F shows the trephination of the central cornea is carried out; FIG. 8G shows the tightening the anchoring sutures thereby displacing the keratoprosthesis so that it will be approximated to the native corneal remnant, facilitating its insertion; FIG. 8H shows how the optical zone is inserted into the trephined space using the snapper tool; FIG. 8I shows the bio-integrating peripheral skirt is laid on the bare sclera and the conjunctiva and tenon are put back and sutured to their position; FIG. 8J shows that the viscoelastic is replaced with BSS (balanced saline solution) in the implanted eye.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A surgical procedure for implanting a keratoprosthesis in a subject in need there of comprising the steps of:
   (1) providing a kit comprising: a keratoprosthesis comprising: (a) a central optical core comprising a central optical lens having an anterior surface, a posterior surface and a radius/diameter; and (b) a peripheral skirt around said central optical core, comprising at least one biocompatible polymer and having a width capable of being placed under a conjunctiva and above a sclera of an eye of a subject in need thereof; wherein said central optical core comprises an anterior rim extending from the anterior surface and a posterior rim extending from the posterior surface; wherein said anterior rim comprises at least two suturing holes and at least two access ports; and wherein said posterior rim comprises at least two extended flanges; and a marking tool comprising a polymeric surface in the shape of said central optical core, having bumps protruding below the polymeric surface, located at the positions of said at least two suturing holes, at least two access ports of the central optical core and a trephination edge;

(2) performing a 360 degree peritomy in an eye of said subject;
(3) performing epithelial debridement;
(4) marking the center of the cornea with a surgical marker;
(5) marking the suturing and access ports on the eye of the subject using the marking tool of the kit using the mark of the center of the cornea for reference;
(6) pre-placing of corneal anchoring suture threads in the marked suturing holes;
(7) intra-cameral injection of epinephrine and (OVD) ophthalmic viscosurgical device;
(8) trephination and removal of central diseased cornea;
(9) approximation of keratoprosthesis of the invention by tying of sutures made in the eye with the suturing holes in the keratoprosthesis;
(10) OVD exchange with balanced salt solution;
(11) tying closure of said conjunctiva of said eye of a subject over the peripheral skirt and rim with sutures.

2. A surgical procedure according to claim 1, wherein said anterior rim comprises at least three suturing holes.

3. A surgical procedure according to claim 1, wherein said suturing holes are located at predetermined distance from each other on the anterior rim.

4. A surgical procedure according to claim 1, wherein said anterior rim comprises at least three access ports.

5. A surgical procedure according to claim 1, wherein said access ports are located at predetermined distances from each other on the anterior rim.

6. A surgical procedure according to claim 1, wherein said anterior rim further comprises at least one biocompatible polymer.

7. A surgical procedure according to claim 1, wherein said posterior rim comprises at least three extended flanges.

8. A surgical procedure according to claim 1, wherein said extended flanges are located at equivalent distances from each other on the posterior rim.

9. A surgical procedure according to claim 1, wherein said central optical lens has a radius/diameter of at least 3 mm.

10. A surgical procedure according to claim 1, wherein said anterior rim has a width of at least 1 mm.

11. A surgical procedure according to claim 1, wherein said posterior rim has a width of at least 1 mm.

12. A surgical procedure according to claim 1, wherein said peripheral skirt has a width of at least 3 mm.

* * * * *